United States Patent [19]

Lin et al.

[11] Patent Number: 4,526,992

[45] Date of Patent: Jul. 2, 1985

[54] SYNTHESIS OF SUBSTITUTED DIOXOLANES BY DIRECT OXIDATION OF OLEFINS OVER MOLYBDENUM 8-HYDROXYQUINOLINE

[75] Inventors: Jiang-Jen Lin, Round Rock; John R. Sanderson, Austin, both of Tex.

[73] Assignee: Texaco, Inc., White Plains, N.Y.

[21] Appl. No.: 662,316

[22] Filed: Oct. 18, 1984

[51] Int. Cl.$^3$ ............................................. C07D 317/00
[52] U.S. Cl. .................................... 549/430; 549/524; 568/479; 557/57
[58] Field of Search .......................................... 549/430

[56] References Cited

U.S. PATENT DOCUMENTS 2,861,081  11/1958  Petrie .................................. 549/430
3,544,599   4/1968  Sze et al. ............................ 549/430

*Primary Examiner*—Ethel G. Love
*Attorney, Agent, or Firm*—Jack H. Park; Kenneth R. Priem; David L. Mossmann

[57] ABSTRACT

The synthesis of substituted dioxolanes by direct oxidation of olefins over a molybdenum 8-hydroxyquinoline catalyst in the presence of water is described. An organic solvent such as chlorobenzene may also be employed. Water is essential to the reaction to make the dioxolanes, otherwise olefin oxides are produced. Hence, 4-methyl-1,3-dioxolane and 2,4-dimethyl-1,3-dioxolane were prepared from propylene oxidation, and three isomers of 2,4,5-trimethyl-1,3-dioxolane were prepared from 2-butene oxidation.

12 Claims, No Drawings

SYNTHESIS OF SUBSTITUTED DIOXOLANES BY DIRECT OXIDATION OF OLEFINS OVER MOLYBDENUM 8-HYDROXYQUINOLINE

CROSS-REFERENCE TO A RELATED APPLICATION

This application is related to U.S. patent application Ser. No. 662,317, filed of even date which relates to the oxidation of olefins over molybdenum 8-hydroxyquinoline.

BACKGROUND OF THE INVENTION

1. Field of the Invention

The invention relates to the catalytic oxidation of olefins to substituted dioxolanes, and more particularly relates to the catalytic oxidation of olefins to substituted dioxolanes over molybdenum catalysts.

2. Other Methods in the Field

The reaction of unsaturated hydrocarbons or olefins with oxygen to produce olefin oxides or alkane epoxides is well known. Such a reaction is even known to occur non-catalytically. See, for example, U.S. Pat. No. 4,380,659 to Solomon which teaches olefin oxidation in the presence of a methyl formate solvent.

However, most of the procedures involve the use of a catalyst. U.S. Pat. No. 3,957,690 discloses a heterogeneous catalyst for the direct oxidation of propylene which may involve oxides of one or more of the following elements: scandium, yttrium, indium, gallium, thallium, rare earth elements of the lanthanide group, silver, vanadium, molybdenum, tungsten, bismuth, manganese and tantalum.

Olefins having four carbon atoms, the butenes, have also been paid much attention. For example, D. J. Hucknall in *Selective Oxidation of Hydrocarbons*, Academic Press: New York, 1974, pp. 96-97, teaches that the oxidation of butenes to carbonyl compounds is known to occur over such catalysts as copper(I) oxide, $SnO_2$—$MoO_3$ and $Co_3O_4$—$MoO_3$. A process for the oxidation of butenes and isobutylene in the presence of trivalent cobalt and a carbonyl compound is taught in European patent application 41,726. The liquid phase oxidation of lower olefins such as 1-butene and 2-butene in the presence of no catalyst, azobisisobutyronitrile, calcium oxide, cobaltic acetylacetonate, cobalt naphthenate, magnesium oxide and mixtures thereof was explored by W. F. Brill, et al. in "The Liquid Phase Oxidation of the Lower Olefins," *J. Org. Chem.*, Vol. 29, 1964, pp. 140-143. U.S. Pat. No. 4,390,738 reveals a process for the oxidation of olefinic compounds (especially those with 2-4 carbons) to olefin oxides or derivatives thereof in the presence of a catalyst containing copper bonded to a peroxy group.

Higher molecular weight olefins may also be oxidized catalytically as seen in F. F. Mayo, et al., "Oxidation of Organic Compounds," Vol. I (Advances in Chemistry Series 75), Amer. Chem. Soc., Washington, DC, 1968, pp. 78-92, where $C_{15}$ to $C_{18}$ α-olefin oxidations are taught. Trialkyl ethylene hydrocarbons may be oxidized with the salt of a heavy metal of Groups VI and VIII of the Periodic Table, such as cobalt naphthenate, cobalt stearate, cobalt acetate, cobalt toluate, manganese naphthanate, manganese acetate, ferrous naphthenate, ferrous acetate, ferrous phthalocyanine and mixtures thereof according to U.S. Pat. No. 3,007,944 to Amir. British Pat. No. 1,483,354 discloses a process for the catalytic oxidation of an acyclic or cyclic mono- or diolefin with oxygen to form epoxy-alcohols in the presence of organovanadium complexes. Similarly, cyclic olefins are oxidized in the presence of vanadium complexed with acetylacetonate and azobisisobutyronitrile using the methods of K. Kaneda, et al., "Direct Epoxy Alcohol Synthesis from Cyclic Olefins Using $O_2$ and VO(acac)$_2$-AIBN Catalyst System," *J. Org. Chem.* (1980), Vol. 45, pp. 3004-3009.

Further, S. Ito, et al. of "[Fe$_3$O(OCOR)$_6$L$_3$]$^+$-Catalyzed Epoxidation of Olefinic Alcohol Acetates by Molecular Oxygen," *J. Amer. Chem. Soc.* (1982), Vol. 104, pp. 6450-6452, teach the oxidation of complicated olefins in the presence of iron complex catalysts. 1-Octene, neat or in tetrachloroethane, reacts with oxygen in the presence of cyclic adducts of peroxobis(triphenylphosphine) platinum with carbon dioxide or hexafluoroacetone to produce the expected autoxidation products and 2-octanone as revealed by W. F. Brill, "Carbon Dioxide and Hexafluoroacetone Adducts of Peroxobis(triphenylphosphine) platinum in the Oxidation of 1-Octene," *J. Molecular Catalysis* (1983), Vol. 19, pp. 69-79.

In particular, molybdenum compounds have attracted attention as catalysts. Note the use of molybdyl-(V)-octaethylporphyrin-hydroxide in the article by M. Baccouche, et al. entitled, "Metallo-porphyrin Catalysed Epoxidations with Molecular Oxygen," *J.C.S. Chem. Comm.* (1977), pp. 821-822. A. F. Noels, et al., "Homogeneous Catalysts by Transition Metal Complexes. Selective Oxidation of Cyclohexene by Mixed-Catalysts Containing Rhodium(II) Complexes," *J. Organometallic Chemistry*, Vol. 166 (1979), pp. 79-86, reveal the oxidation of cyclohexene in the presence of molybdenum acetylacetonate and molybdenum hexacarbonyl.

Lower olefins such as propylene may also be oxidized in the presence of various molybdenum catalysts, such as $CoMoO_4 \cdot V_2O_5$, Sn/Mo oxides, Sn/Mo/Fe oxides among others as taught by T. G. Alkhazov, et al. in "Catalytic Oxidation of Propylene," *Russian Chem. Reviews*, (1982), Vol. 51, No. 6, pp. 542-551. J. Rouchaud, et al. in "Structure et Activite Catalytique Epoxydante des Chelates du Cation Molybdyle," *Bulletin de la Societe Chimique de France* (1969), No. 7, pp. 2294-2295, reveals the oxidation of propylene in the presence of molybdenum chelates. Several azo-compound chelates of $MoO_2^{2+}$, $Wo_2^{2+}$, $Co^{2+}$, $Cr^{3+}$ and $Cu^{2+}$ were used as catalysts in the oxidation of propylene by molecular oxygen according to J. Rouchaud, et al. in "Catalysis by Chelates of Transition Elements of the Liquid Phase Oxidation of Propylene," *J. of Catalysis* (1970), Vol. 19, pp. 172-175. See also the use of molybdenum catalysts for the direct oxidation of propylene by J. E. Lyons, "Up Petrochemical Value by Liquid Phase Catalytic Oxidation," *Hydrocarbon Processing*, (November 1980), pp. 107-119, especially page 117 which teaches $MoO_5$, Mo(acetylacetone)$_3$ and $MoO_2$-(acetylacetonate)$_2$.

Higher olefins are also known to be oxidized using molybdenum catalysts. For example, $MoO_2$-(acetylacetonate)$_2$ and $MoO_2$ are used to catalyze the oxidation of octene in D. Rothe, et al., "Uber die Katalysierte Flussigphasen Oxidation von cis- und trans-Oct-4-en," *J. Prakt. Chemie* (1982), Vol. 324, No. 4, pp. 596-608. Dicyclopentadiene is oxidized over similar catalysts in D. Schnurpfeil, "Katalysierte Flussigphasenoxidation von Dicyclopentadine," *J. Prakt. Chemie* (1983), Vol. 325, No. 5, pp. 842–847.

The compound used as catalyst in this invention, molybdenum 8-hydroxyquinoline, is well known, but not as a catalyst. 8-Hydroxyquinoline has been studied extensively as an extracting agent, such as to recover molybdenum from sea water. See, for example, Chem. Abstracts 100:150025(18), 97:200304(24), 91:145812(18) and 70:14899 (4).

No literature references are known for the direct synthesis of dioxolanes from simple olefins, such as propylene and 2-butene.

SUMMARY OF THE INVENTION

The invention concerns a process for the synthesis of substituted dioxolanes via direct oxidation by reacting an olefin with oxygen in the presence of water and a molybdenum 8-hydroxyquinoline catalyst.

DETAILED DESCRIPTION OF THE PREFERRED EMBODIMENTS

A number of olefins can be directly oxidized according to the method of this invention. The olefinically unsaturated compounds may be substituted and unsubstituted aliphatic and alicyclic olefins which may be hydrocarbons, esters, alcohols, ketones, ethers and the like. It is expected that the process would be particularly useful in oxidizing compounds having 3 to 18 carbon atoms and at least one double bond situated in an alpha position, an internal position or a vinylidene position. Representative compounds include propylene, normal butylene, isobutylene, 2-butene, pentenes, methyl pentenes, hexenes, octenes, dodecenes, such as 1-dodecene, tetradecenes, such as 7-tetradecene, cyclohexene, substituted cyclohexenes, butadiene, styrene, substituted styrenes, vinyl toluene, vinyl cyclohexane, phenyl cyclohexenes, cyclohexenes, and the like. Olefins having substituents containing halogens, oxygen, sulfur and the like may be used. In general, all olefinic materials oxidized by previous methods could probably be used in connection with this process including olefinically unsaturated polymers.

Of course, oxygen as a co-reactant must be present in the molecular $O_2$ form either as a pure gas or as part of an air stream. Surprisingly, water must be present also to give the dioxolanes instead of the epoxides which would result if the water was absent. The amount of water present in the olefin reactant can be 1 to 50%, preferably 10 to 30%. Most preferably, a stoichiometric amount of water to olefin is used.

As noted, the catalyst for the invention is molybdenum 8-hydroxyquinoline, abbreviated as Mo8-HQ. This compound has not been reported as having catalytic activity before now. The material is readily synthesized by reacting 8-hydroxyquinoline with molybdenum in a free element form or in a salt form. See Example 16. The Mo8-HQ catalyst is normally a solid and is somewhat soluble in organic solvents. Other hydroxyquinoline complexes of molybdenum are also expected to be useful in the method of this invention.

The reaction of this invention may be schematically represented as follows,

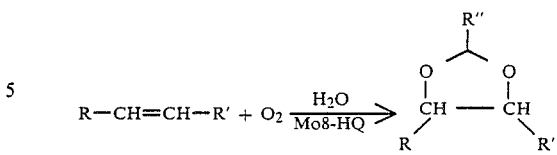

where R, R' and R" are independently hydrogen or alkyl groups of 1 to 16 carbon atoms. R and R' could even be connected so that the olefin is a cyclic olefin. Both cis and trans forms of chiral center containing dioxolanes are formed.

In the case of propylene oxidation, 4-methyl-1,3-dioxolane(I) and 2,4-dimethyl-1,3-dioxolane(II) were observed according to the following reaction.

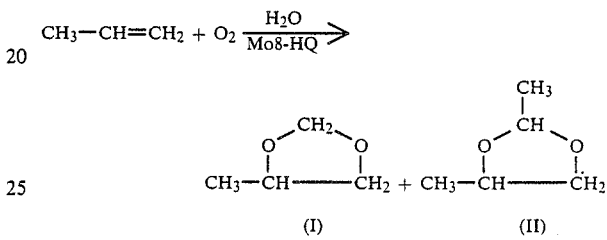

And three stereoisomers of 2,4,5-trimethyl-1,3-dioxolane(III) were obtained in the product mixture from 2-butene oxidations.

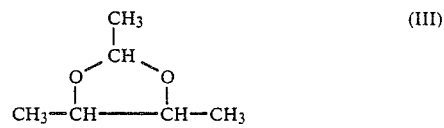

The oxidation reaction of this invention occurs in the liquid phase and may be run batchwise or continuously. Preferably, the temperature range of the reaction is between 100° and 150° C., with an especially preferred range being between 150° and 200° C. The pressure over the reaction should be sufficient to maintain the reactants, except the oxygen, in the liquid phase, preferably from about 50 to 1,000 psi. Inert organic solvents may also be present to help facilitate the reaction. Chlorobenzene is a paticularly preferred solvent. Nitrile solvents such as benzonitrile and acetonitrile will be shown to give poor results, however. When propylene is used as the olefin reactant both 4-methyl-1,3-dioxolane and 2,4-dimethyl-1,3-dioxolane are formed. The addition of paraformaldehyde will enhance the formation of the former while the addition of acetaldehyde will enhance the formation of the latter.

The oxygen, present as a pure gas or part of air, may form the pressure blanket over the reactant mixture or, alternately, may be bubbled through the mixture. The proportion of Mo8-HQ catalyst relative to the olefin is preferably from 10 to 1,000 ppm. The water proportion should be about 20 to 100 ppm based on the olefin proportion.

A number of by-products may be expected in small amounts along with the desired dioxolanes. For example, aldehydes, alkylene oxides, ketones, glycols, alcohols and the like may be formed. The recovery of any desired product may be conducted by any of the well known separation or distillation methods. Preferably, the selectivity to the substituted dioxolanes is at least 40%.

Conversion as defined herein represents the extent of conversion of the reacting olefin to other products. Conversion is expressed as a percentile and is calculated by dividing the amount of olefin consumed during oxidation by the amount of olefin originally charged and multiplying the quotient by 100.

Selectively, as defined herein, is the efficiency in catalyzing a desired oxidation reaction relative to the other undesired conversions. Selectivity is expressed as a percentile and is calculated by determining, for example, the amount of dioxolane formed, divided by the total amount of products formed and multiplying the quotient by 100.

partial pressure was introduced to the autogeneous pressure every 2 minutes. The reaction was terminated at the end of 5 minutes reaction time. The excess gas was vented off slowly and the liquid sample was pressured into a sample bomb. The products were analyzed and identified by GLC, GC-IR and GC-mass spectroscopy. The GLC analysis showed two major product peaks, represented to be 0.7%, and 2.3% in the crude product mixture. These products were identified to be isomers of 2,4-dimethyl-1,3-dioxolane and 4-methyl-1,3-dioxolane by IR and mass spectroscopy. The selectivity to the product isomers was calculated to be about 44% based on converted propylene.

Examples 2 through 8, summarized in Table I, were conducted according to the procedure of Example 1.

TABLE I

| 4-METHYL-1,3-DIOXOLANE (I) AND 2,4-DIMETHYL-1,3-DIOXOLANE (II) SYNTHESIS FROM PROPYLENE[a] | | | | | | | | | | |
|---|---|---|---|---|---|---|---|---|---|---|
| Example | Solvent | Water Addition | Aldehyde Addition | No. of $O_2$ Additions | Conditions | | Propylene[b] Conv., % | Conc., % | | Selectivity, % | |
| | | | | | | | | I | II | Dioxolanes (I + II) | Propylene Oxide |
| 1 | Chlorobenzene 50 g | 10 g | None | 3 | 200° C. | 5 min. | 15 | 0.7 | 2.3 | 44 | 0 |
| 2 | Chlorobenzene 50 g | 20 g | None | 3 | 200° C. | 5 min. | 11 | 0.8 | 1.9 | 62 | 0 |
| 3 | Chlorobenzene 100 g | 20 g | None | 6 | 200° C. | 11 min. | 20 | 0.7 | 1.7 | 53 | 0 |
| 4[c] | Chlorobenzene 50 g | None | None | 3 | 200° C. | 5 min. | 17 | — | — | — | 44 |
| 5 | Chlorobenzene 50 g | 10 g | None | 6 | 174° C. | 11 min. | 19 | 1.7 | 2.4 | 49[d] | 0 |
| 6 | Chlorobenzene 50 g | 10 g | Paraformaldehyde 3.0 g | 6 | 200° | 11 min. | 30 | 1.9 | 3.0 | 42 | 0 |
| 7 | Chlorobenzene 50 g | 2 g | Acetaldehyde 2.5 g | 3 | 200° C. | 5 min. | 19 | 1.2 | 3.3 | 47 | — |
| 8 | Benzonitrile 50 g | 5 g | None | 3 | 200° C. | 5 min. | 16 | 0.6 | 1.5 | 26 | 18 |
| 9 | Acetonitrile 50 g | 10 g | None | 6 | 180° C. | 11 min. | — | <1 | <1 | — | — |

[a]Catalyst: Molybdenum 8-hydroquinoline (0.0055 g), oxygen pressure was 100 psi throughout.
[b]Propylene 31.0 g charged.
[c]Comparative example.
[d]Acetone was the major by-product - ~13%

The dioxolane products from propylene oxidation can be hydrolyzed easily to propylene glycol, formaldehyde and acetaldehyde, which are all well recognized as useful products. The products from butylene oxidation, such as 2,4,5-trimethyl-1,3-dioxolane can be hydrolyzed to 2,3-butene glycol and acetaldehyde. Again, both are useful products. Currently, acetaldehyde is produced via ethylene oxidation (Wacker process). 2,3-Butene glycol might be useful for polymers although 1,4-butane diol is currently used in polyester synthesis.

The invention is further illustrated by the following examples which are not intended to limit the scope of the invention, but which are presented as actual representations of various embodiments of the invention.

EXAMPLE 1

To a 300 ml stainless steel autoclave were charged molybdenum 8-hydroxyquinoline (5.5 mg), chlorobenzene (50 g) and water (10 g). The reactor was sealed and then charged with propylene (31.0 g). The system was heated to 200° C. At this temperature, 100 psi of oxygen

EXAMPLE 10

To a 300 ml stainless steel autoclave were charged molybdenum 8-hydroxyquinoline (5.5 mg), chlorobenzene (50 g) and water (10 g). The reactor was sealed and then charged with a mixture of cis- and trans-2-butene (31 g). The system was heated to 180° C. At this temperature, 100 psi of oxygen partial pressure was introduced to the autogeneous pressure at every 6 minutes. The reaction was terminated at the end of 30 minutes reaction time. The excess gas was vented off slowly and the liquid sample was pressured into a sample bomb. The products were analyzed and identified by GLC, GC-IR and GC-mass spectroscopy. The GLC showed three major product peaks, represented to be 4.0%, 4.1% and 1.0% in the crude product mixture. These three products were identified to be three isomers of 2,4,5-trimethyl-1,3-dioxolane by IR and mass spectroscopy. The selectivity to the three product isomers was calculated to be about 68% based on converted 2-butenes.

Examples 11 through 15 were conducted as Example 10, except for the changes shown in Table II.

TABLE II

| 2,4,5-TRIMETHYL-1,3-DIOXOLANE SYNTHESIS FROM 2-BUTENE DIRECTLY[a] | | | | | | | |
|---|---|---|---|---|---|---|---|
| Example | (grams used) | Solvent Used | Conv., % | Product Conc., % | Selectivities, % | | |
| | | | | | Dioxolane[b] | Acetaldehyde | 2-Butene Oxide |
| 11[c] | Mo—8HQ 0.0055 g | Chlorobenzene 50 g | 54[d] | ~0 | ~0 | 9 | 61 |

TABLE II-continued
2,4,5-TRIMETHYL-1,3-DIOXOLANE SYNTHESIS FROM 2-BUTENE DIRECTLY[a]

| Example | (grams used) | Solvent Used | | Conv., % | Product Conc., % | Selectivities, % Dioxolane[b] | Acetaldehyde | 2-Butene Oxide |
|---|---|---|---|---|---|---|---|---|
| 10 | Mo—8HQ 0.0055 g | Chlorobenzene + H₂O | 50 g 10 g | 25[c] | 9.1 | 68 | 0 | 0 |
| 12 | None | Chlorobenzene + H₂O | 50 g 10 g | 25[c] | 7.6 | ~60 | 0 | 0 |
| 13 | Mo—8HQ 0.0055 g | Chlorobenzene + H₂O | 50 g 15 g | 24[e] | 7.8 | 65 | ~0 | 0 |
| 14 | Mo—8HQ 0.0055 g | Chlorobenzene + H₂O | 50 g 5 g | 22[e] | 6.2 | 50 | 0 | 11 |
| 15 | Mo—8HQ 0.0055 g | Acetonitrile + H₂O | 50 g 10 g | — | 0 | 0 | 12 | 32 |

[a]All examples used 100 psi partial pressure O₂, added 5 times; 180° C. reaction temperature for 0.5 hour.
[b]Mixtures of three isomeric 2,4,5-trimethyl-1,3-dioxolane.
[c]Comparative example.
[d]2-Butene charged: 31 g.
[e]2-Butene charged: 47 g.

EXAMPLE 16

This example will illustrate the preparation of the molybdenum 8-hydroxyquinoline catalyst used in all previous examples.

To a 500 ml distilling flask equipped with a magnetic stirring bar, thermometer, condenser and water take off adapter were added 18 g (1 mole eq.) of ammonium molybdate (powdered), 27 g (2 mole eq.) of 8-hydroxyquinoline and 250 ml. of n-butanol. The white slurry was heated to reflux temperature (about 114° C.) and water and ammonia were evolved. A small amount of n-butyl alcohol, water and lights was removed occasionally from the water trap to prevent lowering of the reflux temperature, approximately 40 ml was collected. After one hour at reflux, the yellow crystalline solid which had formed was washed with methanol and dried in air under aspirator vacuum. Thirty-four grams of light yellow, grainy crystals were recovered. By atomic absorption analysis they were found to contain 34.433 wt.% molybdenum which would suggest that Structure II was more likely than Structure I.

Structure I — Calculated Mo content for Structure I was 23.1 wt. %.

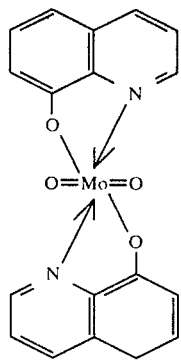

Structure II — Calculated Mo content for Structure II was 35.4 wt. %

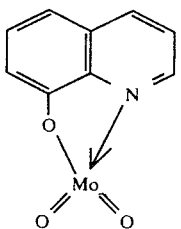

Many modifications may be made by one skilled in the art in this invention without departing from the spirit and scope thereof which are defined only in the appended claims. For example, the temperature, pressure, reactant proportions or catalyst proportions could be modified to optimize the dioxolane results.

We claim:

1. A process for the synthesis of dioxolanes via direct oxidation comprising
    reacting an olefin with oxygen in the presence of water and a molybdenum 8-hydroxyquinoline catalyst to produce substituted dioxolanes.

2. The process of claim 1 in which the olefin has from 3 to 18 carbon atoms.

3. The process of claim 1 in which the reaction is conducted at a temperature in the range of 100° to 250° C. and at a pressure in the range of 50 to 1,000 psi.

4. The process of claim 1 in which the catalyst concentration is between 10 and 1,000 ppm based on the olefin proportion.

5. The process of claim 1 in which the selectivity to the substituted dioxolanes is at least 40%.

6. The process of claim 1 in which the water proportion is 1 to 50 wt.% based on the olefin present.

7. The process of claim 1 in which chlorobenzene is present with the water.

8. A process for the synthesis of dioxolanes via direct oxidation comprising
    reacting an olefin having 3 to 18 carbon atoms with oxygen in the presence of water, chlorobenzene and a molybdenum 8-hydroxyquinoline catalyst at a temperature in the range of 100° to 250° C. and at a pressure in the range of 50 to 1,000 psi to produce substituted dioxolanes.

9. The process of claim 8 in which the catalyst concentration is between 10 and 1,000 ppm based on the olefin proportion.

10. The process of claim 8 in which the selectivity to the substituted dioxolanes is at least 40%.

11. The process of claim 8 in which the water proportion is 1 to 50 wt.% based on the olefin present.

12. A process for the synthesis of dioxolanes via direct oxidation comprising
    reacting an olefin selected from the group consisting of propylene and 2-butene with oxygen in the presence of 1 to 50 wt.% water, chlorobenzene and 10 to 1,000 ppm, based on the olefin, of a molybdenum 8-hydroxyquinoline catayst at a temperature in the range of 130° to 250° C. and at a pressure in the range of 50 to 1,000 psi to give a selectivity to the substituted dioxolanes of at least 40%.

* * * * *